United States Patent
Hloucha et al.

(10) Patent No.: US 8,920,786 B2
(45) Date of Patent: *Dec. 30, 2014

(54) SHAMPOO COMPOSITION HAVING IMPROVED CARE PROPERTIES

(71) Applicant: Cognis IP Management GmbH, Dusseldorf (DE)

(72) Inventors: Matthias Hloucha, Köln (DE); Hans-Martin Haake, Erkrath (DE); Michael Muller, Dietenheim (DE); Esther Küsters, Düsseldorf (DE); Jasmin Menzer, Monheim (DE); Wolf Eisfeld, Langenfeld (DE); Werner Seipel, Hilden (DE); Hermann Hensen, Haan (DE); Axel Bottcher, Kaarst (DE); Esther Ricarda Reinhardt, Kaiserslautern (DE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/686,295

(22) Filed: Nov. 27, 2012

(65) Prior Publication Data

US 2013/0149272 A1 Jun. 13, 2013

Related U.S. Application Data

(63) Continuation of application No. 12/665,368, filed as application No. PCT/EP2008/004801 on Jun. 14, 2008, now Pat. No. 8,343,470.

(30) Foreign Application Priority Data

| Jun. 19, 2007 | (EP) | 07011967 |
| Sep. 27, 2007 | (DE) | 10 2007 046 575 |
| Apr. 3, 2008 | (DE) | 10 2008 017 032 |
| Apr. 3, 2008 | (DE) | 10 2008 017 034 |
| May 7, 2008 | (DE) | 10 2008 022 433 |
| May 21, 2008 | (DE) | 10 2008 024 570 |

(51) Int. Cl.
*A61Q 5/02* (2006.01)
*A61K 8/06* (2006.01)
*A61K 8/60* (2006.01)
*A61K 8/73* (2006.01)
*A61K 8/81* (2006.01)
*A61K 31/01* (2006.01)
*A61Q 5/12* (2006.01)
*A61Q 19/10* (2006.01)

(52) U.S. Cl.
CPC ........... *A61K 8/068* (2013.01); *A61K 8/604* (2013.01); *A61K 8/731* (2013.01); *A61K 8/817* (2013.01); *A61K 31/01* (2013.01); *A61Q 5/02* (2013.01); *A61Q 5/12* (2013.01); *A61Q 19/10* (2013.01); *A61K 8/737* (2013.01); *A61K 2800/5426* (2013.01)
USPC ........... 424/70.24; 424/70.11; 424/70.19; 424/70.21

(58) Field of Classification Search
None
See application file for complete search history.

(56) References Cited

U.S. PATENT DOCUMENTS

| 5,753,241 | A | 5/1998 | Ribier et al. |
| 6,180,117 | B1 | 1/2001 | Berthiaume et al. |
| 6,391,834 | B1 * | 5/2002 | Schelges et al. ............ 510/123 |
| 6,544,530 | B1 | 4/2003 | Friedman |
| 7,811,594 | B2 | 10/2010 | Schreiber et al. |
| 7,897,779 | B2 | 3/2011 | Berg-Schultz et al. |
| 7,910,119 | B2 | 3/2011 | Allef et al. |
| 8,343,470 | B2 * | 1/2013 | Hloucha et al. ............ 424/70.19 |
| 2006/0165639 | A1 | 7/2006 | Gauweiler et al. |
| 2008/0020057 | A1 | 1/2008 | Niebauer et al. |

FOREIGN PATENT DOCUMENTS

| DE | 102 41 296 | 3/2004 |
| DE | 103 54 116 | * 6/2005 |
| DE | 10 2004-030885 | 2/2006 |
| WO | WO 99/53889 | 10/1999 |
| WO | WO 2005/020938 | 3/2005 |
| WO | WO 2006/000257 | 1/2006 |

* cited by examiner

*Primary Examiner* — Jyothsna Venkat
(74) *Attorney, Agent, or Firm* — Servilla Whitney LLC

(57) ABSTRACT

The invention relates to a cosmetic preparation that contains (a) at least one surfactant selected from anionic, zwitterionic or amphoteric surfactants, (b) a microemulsion and (c) at least one cationic polymer.

5 Claims, No Drawings

SHAMPOO COMPOSITION HAVING IMPROVED CARE PROPERTIES

CROSS REFERENCE TO RELATED APPLICATIONS

This application is a continuation of U.S. application Ser. No. 12/665,368, filed Dec. 18, 2009, which is the National Phase entry of PCT/EP2008/004801, filed Jun. 14, 2008, which claims priority to European patent application number EP07011967.2 filed Jun. 19, 2007; German patent application number 10 2007 046 575.2, filed Sep. 27, 2007; German patent application number 10 2008 017 032.1, filed Apr. 3, 2008; German patent application number 10 2008 017 034.8, filed Apr. 3, 2008; German patent application number 10 2008 022 433.2, filed May 7, 2008; and German patent application number 10 2008 024 570.4, filed May 21, 2008, all of which are incorporated herein by reference in their entireties.

FIELD OF THE INVENTION

The invention is in the field of cosmetic compositions for conditioning skin and hair which comprise microemulsions and polymers.

BACKGROUND OF THE INVENTION

After washing, skin and hair often feel rough and brittle, particularly if they have already been predamaged by environmental effects. Moreover, hair can also be damaged by coloring or perming and after hair washing is then often characterized by a dry straw-like feel.

Consequently, in shampoo compositions, conditioners are often used which are intended to counteract these disadvantages. Shampoo compositions are therefore often found which comprise silicones as conditioners. However, these can attach irreversibly to the hair and thus for their part cause negative effects on the feel, and in the worst case may even cause problems during the coloring and perming of the hair.

Also suitable as conditions in these cosmetic preparations are oils and waxes. However, these are not as pronounced as the aforementioned silicones in their effect by a long way. Moreover, as a result of using these conditioners, only cloudy formulations are possible and/or these oils and waxes can in any case only be stabilized in the preparations in small amounts.

SUMMARY OF THE INVENTION

The object of the present invention was therefore to provide cosmetic compositions whose conditioning properties correspond to those of silicone-containing preparations or in the best case scenario even surpass these.

Surprisingly, it has been found that a cosmetic preparation comprising (a) at least one surfactant selected from anionic, zwitterionic or amphoteric surfactants, (b) a microemulsion and (c) at least one cationic polymer achieves the aforementioned object.

The incorporation of a microemulsion as component (b) of the preparations according to the invention facilitates the transparent and stable incorporation of relatively large amounts of oil bodies, which then synergistically with the cationic polymers of component (c) in the composition, stabilized by the surfactants of component (a), bring about the exceptional conditioning properties of the preparation.

DETAILED DESCRIPTION OF THE INVENTION

Surfactants

As component (a), anionic, zwitterionic or amphoteric surfactants may be present. Typical examples of anionic surfactants are soaps, alkylbenzenesulfonates, alkanesulfonates, olefinsulfonates, alkyl ether sulfonates, glycerol ether sulfonates, a-methyl ester sulfonates, sulfo fatty acids, alkyl sulfates, fatty alcohol ether sulfates, glycerol ether sulfates, alkyl ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates, alkyl oligoglucoside carboxylates, protein fatty acid condensates (in particular vegetable products based on wheat) and alkyl (ether) phosphates. If the anionic surfactants contain polyglycol ether chains, these may have a conventional homolog distribution, but preferably have a narrowed homolog distribution. Typical examples of amphoteric or zwitterionic surfactants are alkylbetaines, alkylamidobetaines, aminopropionates, aminoglycinates, imidazoliniumbetaines and sulfobetaines. Particular preference is given to a combination of alkyl ether sulfate and cocamidopropylbetaine, and very particular preference is given to a combination of laureth sulfate and cocamidopropylbetaine.

Microemulsion

The microemulsions of component (c) preferably have an average particle size of less than 1 μm. As component (b) of the present invention, preference is given to using microemulsions based on alkyl polyglycosides.

These emulsions are prepared by initially preparing, in a first step, a microemulsion comprising at least 10-20% by weight of an alkyl (oligo)glycoside of the general formula $R^1O-[G]_p$ in which $R^1$ is an alkyl and/or alkenyl radical having 4 to 22 carbon atoms, G is a sugar radical having 5 or 6 carbon atoms and p is numbers from 1 to 10, and 4-10% by weight of an ester of glycerol with a saturated or unsaturated fatty acid of chain length C12-C22, and 5-30% by weight of an oil body and the remainder to 100% by weight of water.

Microemulsions are firstly understood as meaning all macroscopically homogeneous, optically transparent, low viscosity and in particular thermodynamically stable mixtures of two immiscible liquids and at least one nonionic or one ionic surfactant. The average particle sizes of the microemulsions are usually below 100 nm, they have a high transparency and are stable against visible phase separation upon centrifugation at 2000 rpm for at least 30 minutes.

The preparation of the microemulsions preferably takes place simply by mixing the oil phase with the other oil-soluble ingredients, heating the oil phase to above the melting point of all of the constituents and then adding the aqueous surfactant-containing phase. The thermodynamically stable microemulsion is then formed spontaneously, if appropriate it also being necessary to stir a little.

The microemulsion comprises a sugar surfactant, namely an alkyl (oligo)glycoside (also referred to below as "APG") as obligatory constituents. Within the context of the present teaching, alkyl and/or alkenyl oligoglycosides conform here to the formula $R^1O-[G]_p$ in which $R^1$ is an alkyl and/or alkenyl radical having 4 to 22 carbon atoms, G is a sugar radical having 5 or 6 carbon atoms and p is numbers from 1 to 10. They can be obtained by the relevant methods of preparative organic chemistry. The alkyl and/or alkenyl oligoglycosides may be derived from aldoses or ketoses having 5 or 6 carbon atoms, preferably from glucose. The preferred alkyl and/or alkenyl oligoglycosides are thus alkyl and/or alkenyl oligoglucosides. The index number p in the general formula (I) indicates the degree of oligomerization (DP), i.e. the distribution of mono- and oligoglycosides and is a number between 1 and 10. Whereas p in a given compound must always be an integer and here can in particular assume the values p=1 to 6, the value p for a specific alkyl oligoglycoside is an analytically determined calculable quantity which in most cases is a fraction. Preference is given to using alkyl and/or alkenyl oligoglycosides having an average degree of oligomerization p of from 1.1 to 3.0. From an applications point of view, preference is given to those alkyl and/or alkenyl oligoglycosides whose degree of oligomerization is less than 1.7 and is in particular between 1.2 and 1.5. APGs are present in the microemulsions according to the present invention in amounts between 10 and 20% by weight, in each case based on the total amount of the microemulsion. Particular preference is given here to amounts in the range from 14 to 19% by weight.

Furthermore, esters of fatty acids of chain length C12-C22 with glycerol are present in the emulsions. Preference is given here to using monoesters of glycerol, with monoesters of glycerol with unsaturated linear fatty acids in particular being suitable. Within the context of the invention, particular preference is given to glycerol monooleate. These glycerol esters are present in the microemulsions in amounts of from 4 to 10% by weight, preferably 5 to 9% by weight—in each case based on the total weight of the microemulsion.

Finally, the microemulsions also comprise an oil body, thus a non-water-soluble organic phase in amounts of from 5 to 30% by weight. Here, particularly preferred oil phase are selected from the group of Guerbet alcohols based on fatty alcohols having 6 to 18 carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, esters of linear $C_6$-$C_{22}$-fatty acids with branched alcohols, esters of $C_6$-$C_{22}$-fatty alcohols and/or Guerbet alcohols with aromatic carboxylic acids, triglycerides based on $C_6$-$C_{10}$-fatty acids, liquid mono-/di-/triglyceride mixtures based on $C_6$-$C_{18}$-fatty acids, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear or branched $C_6$-$C_{22}$-fatty alcohol carbonates, Guerbet carbonates based on fatty alcohols having 6 to 18, preferably 8 to 10, carbon atoms, esters of benzoic acid with linear and/or branched $C_6$-$C_{22}$-alcohols, linear or branched, symmetrical or asymmetrical dialkyl ethers having 6 to 22 carbon atoms per alkyl group, ring-opening products of epoxidized fatty acid esters with polyols, silicone oils and/or aliphatic or naphthenic hydrocarbons, dialkylcyclohexanes and/or silicone oils. However, as oil component it is also possible solid fats and/or waxes. These may also be present in a mixture with the oils specified in the preceding section. Typical examples of fats are glycerides, i.e. solid or liquid vegetable or animal products which consist essentially of mixed glycerol esters of higher fatty acids. Here, mention is to be made in particular of solid mono- and diglycerides, such as, for example, glycerol monooleate or glycerol monostearate. Suitable waxes are, inter alia, natural waxes, such as, for example, candelilla wax, carnauba wax, Japan wax, esparto grass wax, cork wax, guaruma wax, rice germ oil wax, sugar cane wax, ouricury wax, montan wax, beeswax, shellac wax, spermaceti, lanolin (wool wax), uropygial wax, ceresine, ozokerite (earth wax), petrolatum, paraffin waxes, microwaxes; chemically modified waxes (hard waxes), such as, for example, montan ester waxes, sasol waxes, hydrogenated jojoba waxes, and also synthetic waxes, such as, for example, polyalkylene waxes and polyethylene glycol waxes. Tocopherols and essential oils are likewise suitable as oil component.

Hydrocarbons is the term used to refer to organic compounds which consist only of carbon and hydrogen. They include both cyclic and acyclic (=aliphatic) compounds. They comprise both saturated and also mono- or polyunsaturated compounds. The hydrocarbons may be linear or branched. Depending on the number of carbon atoms in the hydrocarbon, the hydrocarbons can be divided into odd-numbered hydrocarbons (such as, for example, nonane, undecane, tridecane) or even-numbered hydrocarbons (such as, for example, octane, dodecane, tetradecane). Depending on the type of branching, the hydrocarbons can be divided into linear (=unbranched) or branched hydrocarbons. Saturated, aliphatic hydrocarbons are also referred to as paraffins.

"Hydrocarbon mixture" is understood as meaning mixtures of hydrocarbons which comprise up to 10% by weight of substances which are not types of hydrocarbons. The % by weight data of the linear C11 and linear C13 hydrocarbons refers in each case to the sum of the hydrocarbons present in the mixture. The non-hydrocarbons present up to 10% by weight are not taken into consideration for this calculation.

The substances which are not types of hydrocarbons and which may be present in the hydrocarbon mixture up to 10% by weight, in particular up to 8% by weight, preferably up to 5% by weight, are, for example, fatty alcohols, which remain as unreacted starting materials in the hydrocarbon mixture.

The term "CX hydrocarbon" encompasses hydrocarbons with a carbon number of X, thus, for example, the term C11 hydrocarbon encompasses all hydrocarbons with a carbon number of 11.

Preference is given to hydrocarbon mixtures where the mixture comprises
(a) 50 to 90% by weight of linear C11 hydrocarbons, preferably n-undecane
(b) 10 to 50% by weight of linear C13 hydrocarbons, preferably n-tridecane
based on the sum of the hydrocarbons.

Furthermore, preference is given to a hydrocarbon mixture which comprises at least 2 different hydrocarbons whose carbon number differs by more than 1, where these 2 different hydrocarbons constitute at least 60% by weight, preferably at least 70% by weight-based on the sum of the hydrocarbons.

The term "2 different hydrocarbons" refers to hydrocarbons with a different carbon number.

This means if the hydrocarbon mixture comprises a hydrocarbon with a carbon number of n (n=integer), then the mixture also comprises at least one further hydrocarbon with a carbon number greater than or equal to n+2 or less than or equal to n−2.

Preferably, n is an odd number, in particular, 7, 9, 11, 13, 15, 17, 19, 21 and/or 23.

Furthermore, the hydrocarbon used may be a hydrocarbon mixture which comprises $^{14}C$ isotope and where the hydrocarbon mixture comprises at least 2 different hydrocarbons whose carbon number differs by more than 1.

A further essential constituent of the microemulsions is water. The water should preferably be demineralized. The microemulsions preferably comprise up to 81% by weight of water. Preferred ranges are amounts from 30 to 80% by weight and in particular from 45 to 65% by weight of water.

Besides the ingredients described above, the microemulsions can also comprise, as additional constituent, fatty alcohols of the general formula $R^2$—OH, where $R^2$ is a saturated or unsaturated, branched or unbranched alkyl or alkenyl radical having 6 to 22 carbon atoms may contain. Typical examples are caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol, and technical-grade mixtures thereof which are produced, for example, during the high-pressure hydrogenation of technical-grade methyl esters based on fats and oils or aldehydes from the Roelen oxo synthesis, and also as monomer fraction during the dimerization of unsaturated fatty alcohols. Preference is given to technical-grade fatty alcohols having 12 to 18 carbon atoms, such as, for example, coconut, palm, palm kernel or tallow fatty alcohol. Particular preference is given to the co-use of cetyl alcohol, stearyl alcohol, arachyl alcohol and behenyl alcohol, and mixtures thereof.

If fatty alcohols are present, they are preferably used in amounts up to 15% by weight, based on the total microemulsion, where the range from 1 to 10% by weight and preferably 2 to 8% by weight may be particularly preferred. According to the invention, these fatty alcohols, which constitute water-insoluble organic constituents, also do not fall under the definition of the oil body.

The microemulsion which is prepared in the first step of the method according to the invention can furthermore also comprise anionic surfactants. Typical examples of anionic surfactants are soaps, alkylbenzenesulfonates, alkanesulfonates, olefinsulfonates, α-methyl ester sulfonates, sulfo fatty acids, alkyl sulfates, alkyl ether sulfates, mono- and dialkyl sulfosuccinates, mono- and dialkyl sulfosuccinamates, sulfotriglycerides, monoglyceride sulfates, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates and protein fatty acid condensates (in particular vegetable products based on wheat).

Within the context of the present invention, preference is given to fatty alcohol ether sulfates, here in particular to those of the general formula $R^3O$—$(CH_2CH_2O)_m SO_3X$, in which $R^3$ is a linear or branched alkyl and/or alkenyl radical having 6 to 22 carbon atoms, n is numbers from 1 to 10 and X is an alkali metal and/or alkaline earth metal, ammonium, alkylammonium, alkanolammonium or glucammonium. Alkyl ether sulfates ("ether sulfates") are known anionic surfactants which are prepared industrially by $SO_3$ or chlorosulfonic acid (CSA) sulfation of fatty alcohol or oxo alcohol polyglycol ethers and subsequent neutralization. Typical examples are the sulfates of addition products of, on average, 1 to 10 and in particular 2 to 5 mol of ethylene oxide onto caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol, and also technical-grade mixtures thereof in the form of their sodium and/or magnesium salts. The ether sulfates here can have either a conventional or a narrowed homolog distribution. Particular preference is given to the use of ether sulfates based on adducts of, on average, 2 to 3 mol of ethylene oxide onto technical-grade $C_{12/14}$- or $C_{12/18}$-coconut fatty alcohol fractions in the form of their sodium and/or magnesium salts.

The microemulsions used in the method according to the invention can also comprise further nonionic, amphoteric and/or cationic surfactants, preferably in amounts of, in total, 1 to 25% by weight, based on the total weight of the emulsion. Typical examples of further nonionic surfactants (besides the alkyl (oligo)glycosides) are, for example, fatty acid N-alkylglucamides, polyol fatty acid esters, sugar esters, sorbitan esters, polysorbates, alcohol ethoxylates and amine oxides. Depending on the preparation, alcohol ethoxylates are referred to as fatty alcohol ethoxylates or oxo alcohol ethoxylates and preferably conform to the formula $R^4O(CH_2CH_2O)_n H$ $R^4$ is a linear or branched alkyl and/or alkenyl radical having 6 to 22 carbon atoms and n is numbers from 1 to 50. Typical examples are the adducts of, on average, 1 to 50, preferably 5 to 40 and in particular 10 to 25, mol of caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol, and also technical-grade mixtures thereof which are produced, for example, during the high-pressure hydrogenation of technical-grade methyl esters based on fats and oils or aldehydes from the Roelen oxo synthesis, and also as monomer fraction in the dimerization of unsaturated fatty alcohols. Preference is given to adducts of from 10 to 40 mol of ethylene oxide onto technical-grade fatty alcohols having 12 to 18 carbon atoms, such as, for example, coconut, palm, palm kernel or tallow fatty alcohol.

Examples of suitable amphoteric and zwitterionic surfactants are alkylbetaines, alkylamidobetaines, aminopropionates, aminoglycinates, imidazolinium betaines and sulfobetaines. Examples of suitable alkylbetaines are the carboxyalkylation products of secondary and in particular tertiary amines. Typical examples are the carboxymethylation products of hexylmethylamine, hexyldimethylamine, octyldimethylamine, decyldimethylamine, dodecylmethylamine, dodecyldimethylamine, dodecylethylmethylamine, $C_{12/14}$-cocoalkyldimethylamine, myristyldimethylamine, cetyldimethylamine, stearyldimethylamine, stearylethylmethylamine, oleyldimethylamine, $C_{16/18}$-tallow-alkyldimethylamine, and technical-grade mixtures thereof. Also suitable are furthermore carboxyalkylation products of amidoamines. Typical examples are reaction products of fatty acids having 6 to 22 carbon atoms, namely caproic acid, caprylic acid, capric acid, lauric acid, myristic acid, palmitic acid, palmoleic acid, stearic acid, isostearic acid, oleic acid, elaidic acid, petroselic acid, linoleic acid, linolenic acid, elaeostearic acid, arachic acid, gadoleic acid, behenic acid and erucic acid, and also technical-grade mixtures thereof, with N,N-dimethylaminoethylamine, N,N-dimethylaminopropylamine, N,N-diethylaminoethylamine and N,N-diethylaminopropylamine, which are condensed with sodium chloroacetate. Preference is given to using a condensation product of $C_{8/18}$-coconut fatty acid N,N-dimethylaminopropylamide with sodium chloroacetate. Furthermore, imidazolinium betaines are also suitable. These substances too are known substances which can be obtained, for example, by cyclizing condensation of 1 or 2 mol of fatty acid with polyfunctional amines, such as, for example, aminoethylethanolamine (AEEA) or diethylenetriamine. The corresponding carboxyalkylation products are mixtures of different open-chain betaines. Typical examples are condensation products of the aforementioned fatty acids with AEEA, preferably imidazolines based on lauric acid or again $C_{12/14}$-coconut fatty acid, which are then betainized with sodium chloroacetate.

Typical examples of cationic surfactants are quaternary ammonium compounds and ester quats, in particular quaternized fatty acid trialkanolamine ester salts.

Particularly preferred microemulsions have the following composition:

| | |
|---|---|
| alkyl (oligo)glycosides | 10 to 20% by weight |
| glycerol fatty acid esters | 4 to 10% by weight |
| oil bodies | 5 to 30% by weight |
| fatty alcohol ether sulfates | 0 to 15% by weight |
| fatty alcohols | 0 to 15% by weight |

The remainder to 100% by weight is then in each case water, if appropriate supplemented by further, optional ingredients.

Cationic Polymers

As component b), the cosmetic compositions of the present patent application comprise cationic polymers. These are preferably selected from the group of homopolymers or copolymers of ester or amide derivatives of acrylic acid or methacrylic acid (e.g. INCI: Polyquaternium-7), homopolymers of methacryloylethyltrimethylammonium chloride (INCI: Polyquaternium-37), quaternary copolymers of hydroxyethylcellulose and diallyldimethyl ammonium chloride (INCI: Polyquaternium-4), polymeric quaternized ammonium salts of hydroxyethylcellulose which have been modified with a trimethylammonium-substituted epoxide (INCI: Polyquaternium-10), depolymerized guar gum derivatives which have been quaternized (INCI: Guar Hydroxypropyl Trimonium Chloride) or quaternized guar derivatives and quaternary copolymers of hydroxyethylcellulose and diallyldimethylammonium chloride. In a preferred embodiment, the cationic polymer (c) is selected from the group which is formed by polyquaternium-7, polyquaternium-10 and cationic guar derivatives. The preparations according to the invention preferably comprise 0.05 to 2% by weight of these cationic polymers.

Preference is given to a cosmetic preparation comprising
(a) alkyl ether sulfates and cocamidopropylbetaine,
(b) a microemulsion comprising
(b1) alkyl oligoglycosides,
(b2) esters of glycerol with a saturated or unsaturated fatty acid of chain length C12-22 and
(b3) oil bodies and
(b4) water, and
(c) a cationic polymer selected from the group which is formed by polyquaternium-7, polyquaternium-10 and cationic guar derivatives.

Particular preference is given to a cosmetic preparation comprising
(a) 5-20% by weight, based on the total composition, of alkyl ether sulfates and cocamidopropylbetain,
(b) 0.5-10% by weight, based on the total composition of a microemulsion comprising (quantitative data for components (b1) to (b4) based on the microemulsion)
(b1) 10-20% by weight of alkyl oligoglycosides,
(b2) 4-10% by weight of esters of glycerol with a saturated or unsaturated fatty acid of chain length C12-22,
(b3) 5-30% by weight of an oil body and
(b4) remainder to 100% by weight of water, and
(c) 0.05-1% by weight, based on the total composition, of a cationic polymer selected from the group which is formed by polyquaternium-7, polyquaternium-10 and cationic guar derivatives.

The present invention further provides a process for producing a cosmetic preparation by stirring
(a) at least one surfactant selected from anionic, zwitterionic or amphoteric surfactants,
(b) a microemulsion and
(c) at least one cationic polymer
with further cosmetic base substances.

EXAMPLES

Firstly a microemulsion with the following composition was prepared by mixing the ingredients (Tables 1 and 2):

TABLE 1

Composition of a microemulsion according to component b) of the invention:

| Substance | INCI | % by weight of active substance |
|---|---|---|
| Plantacare ® 2000 UP | Decyl Glucoside | 17.5 |
| Monomuls ® 90 O 18 | Glyceryl Oleate | 8 |
| Cetiol ® OE | Dicaprylyl Ether | 20 |
| Aqua dem. | | add 100 |

TABLE 2

Composition of a microemulsion according to component b) of the invention:

| Substance | INCI | % by weight of active substance |
|---|---|---|
| Plantacare ® 2000 UP | Decyl Glucoside | 18 |
| Texapon ® NSO | Sodium Laureth Sulfate | 12 |
| Cetiol ® CC | Dicaprylyl Carbonate | 20 |
| Aqua dem. | | add 100 |

Tables 3 and 4 below list various shampoo formulations which have the compositions according to the invention. Examples 1-3, 9 and 11 serve as the comparison.

TABLE 3

Shampoo formulations and wet combability properties (quantitative data in % by weight of active substance)

| Brand product | INCI | 1 | 2 | 3 | 4 | 5 | 6 | 7 | 8 |
|---|---|---|---|---|---|---|---|---|---|
| Texapon ® N70 | Sodium Laureth Sulfate | 9 | 9 | 9 | 9 | 9 | 9 | 9 | 9 |
| Dehyton ® PK 45 | Cocamidopropyl Betaine | 3 | 3 | 3 | 3 | 3 | 3 | 3 | 3 |
| Emulsion as in Table 1 | | 0.00 | 1.78 | 0.00 | 0.36 | 0.89 | 1.78 | 3.57 | 7.14 |
| Dekaquat ® 400 KC | Polyquaternium-10 | 0 | 0 | 0.2 | 0.2 | 0.2 | 0.2 | 0.2 | 0.2 |

TABLE 3-continued

Shampoo formulations and wet combability properties (quantitative data in % by weight of active substance)

| Brand product | INCI | 1 | 2 | 3 | 4 | 5 | 6 | 7 | 8 |
|---|---|---|---|---|---|---|---|---|---|
| Arlypon ® TT | PEG/PPG-120/10 Trimethylolpropane | 0.65 | 0.65 | 0.65 | 0.65 | 0.65 | 0.65 | 0.65 | 0.65 |
| Euxyl ® K 400 | Methyldibromo Glutaronitrile and Phenoxyethanol | 0.1 | 0.1 | 0.1 | 0.1 | 0.1 | 0.1 | 0.1 | 0.1 |
| Aqua dem. | | | | | add 100 | | | | |
| Residual combing work in % | | 100 | 100 | 58 | 46 | 37 | 29 | 33 | 43 |

TABLE 4

Shampoo formulations and wet combability properties (quantitative data in % by weight of active substance)

| Brand product | INCI | 9 | 10 | 11 | 12 |
|---|---|---|---|---|---|
| Texapon ® N70 | Sodium Laureth Sulfate | 9 | 9 | 9 | 9 |
| Dehyton ® PK 45 | Cocamidopropyl Betaine | 3 | 3 | 3 | 3 |
| Emulsion as in Table 1 | | 0.00 | 3.57 | 0.00 | 0.57 |
| Jaguar ® C13 S | Guar Hydroxypropyltrimonium Chloride | 0.2 | 0.2 | — | — |
| Rheocare ® CC7 | Polyquaternium-7 | — | — | 0.2 | 0.2 |
| Arlypon ® TT | PEG/PPG-120/10 Trimethylolpropane | 0.65 | 0.65 | 0.65 | 0.65 |
| Euxyl ® K 400 | Methyldibromo Glutaronitrile and Phenoxyethanol | 0.1 | 0.1 | 0.1 | 0.1 |
| NaCl | | 1 | 1 | 1 | 1 |
| Aqua dem. | | | add 100 | | |
| Residual combing work in % | | 83 | 66 | 100 | 81 |

The investigations with regard to the conditioning properties of the shampoos were carried out in each case on 10 hair tresses in an automated system for determining the wet combing work.

The pretreatment of the hair tresses (12 cm/1 g) from IHIP were carried out in an automated hair treatment system:
- 30 min cleansing with 6% sodium lauryl ether sulfate, pH 6.5, then intensive rinsing of the hair
- 20 min bleaching with a solution of 5% hydrogen peroxide, pH 9.4 (adjusted with ammonium hydroxide solution), then intensive rinsing of the hair
- 30 min drying in a stream of air at 68° C.

Directly prior to the zero measurement, the hair was swollen in water for 30 minutes and then rinsed out using an automatic wet combing-out apparatus for 1 minute. In the automated system for determining the wet and dry combing work, the combing forces during 20 combings were determined and the combing work was calculated by integrating the measured force-displacement curves. Following the zero measurement, the hair was immediately treated with the formulation (0.25 g/g of hair). After a contact time of 5 minutes, rinsing was carried out with the automatic wet combing-out apparatus under standard conditions (38° C., 1 l/minute).

The treatment and the subsequent rinsing was repeated a second time. The comparison measurement (for the zero measurement) was then carried out. The measurements were carried out using the fine comb side of the natural rubber combs. The residual combing work was calculated per tress as follows:

Residual combing work=combing work after product treatment/combing work before product treatment The mean value and the standard deviation were then determined via the quotients for all 10 tresses.

The examples impressively demonstrate the synergistic interaction of polymer and microemulsion, which is apparent from the exceptionally low values for the residual combing work.

The invention claimed is:

1. A silicone-free shampoo composition comprising:
   (a) about 5-20% by weight, based on the composition, anionic surfactant selected from the group consisting of sodium laureth sulfate, sodium lauryl sulfate, sodium lauryl glucose carboxylate/lauryl glucoside, sodium C14-16 olefin sulfonate, and sodium C12-15 pareth-15 sulfonate,
   (b) about 0.5-10% by weight, based on the composition, of a microemulsion comprising:
      (i) about 10-20% by weight, based on the microemulsion, of decyl glucoside,
      (ii) about 4-10% by weight, based on the microemulsion, of glyceryl oleate,
      (iii) about 5-30% by weight, based on the microemulsion, of dicaprylyl ether, and
      (iv) the remainder to 100% by weight, based on the microemulsion, of water; and
   (c) about 0.05-1% by weight, based on the composition, cationic polymer selected from the group consisting of polyquaternium-7, polyquaternium-10 and guar hydroxypropyltrimonium chloride.

2. The shampoo composition of claim 1, wherein component (a) further comprises an amphoteric or zwitterionic surfactant.

3. The shampoo composition of claim 2, wherein the amphoteric or zwitterionic surfactant is cocoamidopropylbetaine.

4. The shampoo composition of claim 1 wherein component (a) comprises a mixture of sodium laureth sulfate and cocoamidopropylbetaine or mixture of sodium lauryl sulfate and cocoamidopropylbetaine.

5. A process for producing the silicone-free shampoo composition of claim 1, comprising stifling with further cosmetic substances the anionic surfactant of step (a), the microemulsion of step (b) and the at least one cationic polymer of step (c).

* * * * *